United States Patent [19]
Contet et al.

[11] Patent Number: 5,750,492
[45] Date of Patent: May 12, 1998

[54] SURFACTANTS BASED ON QUATERNARY AMMONIUM COMPOUNDS PREPARATION PROCESSES SOFTENING BASES AND COMPOSITIONS DERIVED

[75] Inventors: Jean-Pierre Contet, Saint Jean De Moirans; Stéphane Courdavault Duprat, Meylan; Yvan Storet, Veurey-Voroize; Jean-Francois Vindret, Saint Laurent Du Pont, all of France

[73] Assignee: Stepan Europe, France

[21] Appl. No.: 872,357

[22] Filed: Jun. 10, 1997

Related U.S. Application Data

[63] Continuation of Ser. No. 447,219, May 22, 1995, Pat. No. 5,637,743, which is a continuation of Ser. No. 998,566, Dec. 30, 1992, abandoned.

[30] Foreign Application Priority Data

Dec. 31, 1991 [FR] France .................. 91 16479
Mar. 12, 1992 [FR] France .................. 92 03199
Jul. 17, 1992 [FR] France .................. 92 09087

[51] Int. Cl.$^6$ .............. C07C 211/13; C07C 233/36; C07C 233/38; C11D 1/00
[52] U.S. Cl. .......... 510/527; 252/8.63; 510/515; 510/516; 510/517; 510/518; 510/521; 510/522; 510/523; 510/524; 510/510; 510/525; 510/526; 554/52; 554/110; 560/151; 560/169; 560/172; 564/159
[58] Field of Search ............ 554/52, 110; 560/151, 560/769, 172; 564/159; 252/8.63; 510/515, 516, 517, 518, 521, 522, 523, 524, 525, 526, 527

[56] References Cited

U.S. PATENT DOCUMENTS

| | | | |
|---|---|---|---|
| 3,074,815 | 1/1963 | Lee et al. | 117/143 |
| 4,128,485 | 12/1978 | Bauman et al. | 252/8.8 |
| 4,830,771 | 5/1989 | Ruback et al. | 252/8.8 |

FOREIGN PATENT DOCUMENTS 0284036  9/1988  European Pat. Off. .

*Primary Examiner*—Peter O'Sullivan
*Attorney, Agent, or Firm*—McDonnell Boehnen Hulbert & Berghoff

[57] ABSTRACT

Cationic surfactant compound comprising, in the form of a quaternary ammonium salt, a product of condensation between, on the one hand a fraction of saturated or unsaturated fatty acids, or of derivatives of said acids chosen from the group comprising esters, anhydrides and acid chlorides, and on the other hand at least one tertiary amine, characterized in that, in combination:

- the alkyl chains of the tertiary amine together contain from 4 to 12 carbon atoms
- the alkyl chains of the tertiary amine together contain from 1 to 4 functions each chosen from the group comprising hydroxyl and amine functions
- the fatty acids fraction/tertiary amine mole ratio is between 1.85 and 1.40
- the fatty acids each possess a hydrocarbon chain in which the number of carbon atoms is between 5 and 23.

10 Claims, No Drawings

SURFACTANTS BASED ON QUATERNARY AMMONIUM COMPOUNDS PREPARATION PROCESSES SOFTENING BASES AND COMPOSITIONS DERIVED

This is a continuation of application Ser. No. 08/447,819, filed May 22, 1995, now U.S. Pat. No. 5,637,743 which is a continuation of application Ser. No. 07/998,556, filed Dec. 30, 1992, now abandoned The field of the present invention is that of suppling or softening compositions, in particular for textiles, comprising as active agent at least one cationic surfactant of the quaternary ammonium type.

According to the document EP-0,284,036, a product is proposed, in the form of a quaternary ammonium salt, resulting from the condensation between:

- on the one hand a fraction of saturated or unsaturated, linear or branched fatty acids in the form of glycerol esters and preferably glyceride triesters, said fatty acids each possessing a hydrocarbon chain in which the number of carbon atoms is between 5 and 23,
- and on the other hand at least one functionalized tertiary amine in which the alkyl chains together contain at least four carbon atoms and correspond to the following formula (III):

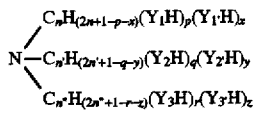

in which:

$4<n+n'n''<11$, $1<p+q+r+x+y=z<3$, with $p+x=1$, $q+y$ and $r+z$ equal to 0 or 1

$Y_1, Y_{1'}, Y_2, Y_{2'}, Y_3, Y_{3'}$ are oxy functional groups.

The fatty acid fraction/tertiary amine mole ratio is preferably equal to 1 in order to obtain a monoesterified condensation product, and equal to 2 in order to obtain a diesterified condensation product. It is preferably in the diester form that the condensation product finds application as a softener and suppling agent for textiles.

The condensation product obtained is usable at relatively high concentrations in concentrated textile softeners. Such a use is impeded, however, by two major drawbacks, that of lack of fluidity and that of lack of stability. And the preparation of compositions having given viscosity and given stability with such products involves the need to lower the concentration of the latter.

The subject of the present invention is a surfactant product for textile softening, of the chemical family identified above, which, even in the absence of complex additives, possesses both good stability and good fluidity or "pourability" at relatively high concentrations.

According to the present invention, it was found that such surfactant compounds could be obtained by the choice of a fatty acid fraction/tertiary amine mole ratio of between 1.85 and 1.40, with tertiary amines in which the alkyl chains contain up to 12 carbon atoms and one to four functions chosen from the group comprising hydroxyl and amine functions.

It was, in effect, found that, for a fatty acid fraction/tertiary amine mole ratio higher than 1.85, the concentrated formulations are less fluid and, most particularly, less stable, and that for the same ratio lower than 1.4, the conditioning and lubricating power is less good.

The fatty acids are in free form or are derived [sic]; in the latter case, the derivatives are chosen from the group comprising esters, anhydrides and acid chlorides, or are alternatively in the form of glycerol esters, and preferably triesters of fatty acids and glycerol.

Preferably, the fatty acid fraction contains at least 50 mol % of saturated or unsaturated, linear $C_{16}$ to $C_{18}$ acids. This enables an acceptable softening power to be preserved.

When $C_{16}/C_{18}$ fatty acid fraction predominantly contains linear $C_{18}$ acids, the fatty acid fraction/tertiary amine mole ratio is preferably between 1.82 and 1.60. When the $C_{16}/C_{18}$ fatty acid fraction predominantly contains linear $C_{16}$ acids, the fatty acid fraction/tertiary amine mole ratio is preferably between 1.85 and 1.66.

When the fatty acid fraction is at least partially unsaturated, the following two embodiments of the present invention are preferred:

- when the $C_{16}/C_{18}$ fatty acid fraction predominantly contains linear $C_{18}$ acids, this fraction possesses an overall unsaturation expressed by an iodine number (according to AFNOR French Standard NF ISO 3961 of February 1990) of between 10 and 33, and in particular between 15 and 33
- when the $C_{16}/C_{18}$ fatty acid fraction predominantly contains linear $C_{16}$ acids, this fraction possesses an overall unsaturation expressed by an iodine number of between 10 and 43, and in particular between 15 and 35.

According to the present invention, it was, in effect, demonstrated that an excessively low unsaturation increased the viscosity and instability of concentrated formulations, and that an excessively high unsaturation decreased the softening and increased the residual odor on storage.

According to another embodiment of the invention, a surfactant compound results from the condensation of a fatty acid fraction with a mixture of a polyhydroxylated tertiary amine and a tertiary amine substituted with a hydroxyl or amine function, this being made in a mole ratio of the first amine to the second equal to at least 2.

In the latter case, when the $C_{16}/C_{18}$ fatty acid fraction predominantly contains linear $C_{16}$ acids, the overall unsaturation of this fraction is less than 45, and in particular less than 35, again expressed by the iodine number of said fraction; when this same $C_{16}/C_{18}$ fatty acid fraction predominantly contains linear $C_{18}$ acids, it possesses an overall unsaturation expressed by an iodine number of less than 33.

A basic molecule of a surfactant according to the invention corresponds to the above generic chemical formula (I),

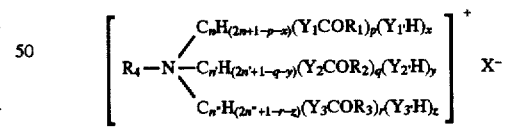

in which:

n, n' and n'' are non-zero integers, the mean of whose sum is equal to at least 4, expressed with reference to one mol of surfactant, p, q, r, x, y and z are integers or zero, $Y_1, Y_{1'}, Y_2, Y_{2'}, Y_3, Y_{3'}$ are functional groups, $R_1, R_2, R_3$ are, respectively, a long alkyl or alkenyl hydrocarbon chain having 5 to 23 carbon atoms $R_4$ is a short alkyl chain having from 1 to 5 carbon atoms, and X is a counterion, and is characterized by the following choice of chemical parameter:

expressed with reference to one mol, the mean of the sum of p, q and r is statistically between 1.85 and 1.40, the mean of said sum of n, n' and n" is statistically equal to not more than 12, expressed with reference to one mol, and the functional groups $Y_1$, $Y_{1'}$, $Y_2$, $Y_{2'}$, $Y_3$, $Y_{3'}$ are each chosen from oxy, N and NH groups and numbering together between 1 and 4.

A preferred surfactant of the invention is that which consists of a mixture of at least two compounds corresponding to the formula (I) in which:

$Y_1$, $Y_{1'}$, $Y_2$, $Y_{2'}$, $Y_3$, $Y_{3'}$ are oxy groups, and (p+q+r) is between 1.82 and 1.60 when the long chains $R_1$, $R_2$, $R_3$ are predominantly $C_{17}$ chains, or is between 1.85 and 1.66 when the long chains $R_1$, $R_2$, $R_3$ are predominantly $C_{15}$ chains.

Another preferred surfactant of the invention is that which consists of a mixture of at least two compounds corresponding to the formula (I) in which:

$Y_1$, $Y_{1'}$, $Y_2$, $Y_{2'}$, $Y_3$, $Y_{3'}$ are oxy groups, and the iodine number expressed with reference to the fatty acids corresponding to $R_1$, $R_2$, $R_3$ is between 15 and 35 when they predominantly contain $C_{15}$ chains, and is between 15 and 33 when they predominantly contain $C_{17}$ chains.

In addition to its stability, the surfactant of the invention is especially advantageous in that its use, even at high concentrations, does not give rise to the discharge of toxic materials into the environment, since the compound of the invention of which it is composed is biodegradable.

Biodegradable is understood to refer both to primary biodegradability, that is to say the loss of surfactant power which must be at least 80% in a static test termed "bottle test", in particular according to AFNOR French Experimental Standard Pr T73280, and to total biodegradability, by monitoring the loss of at least 80% of the dissolved organic carbon, for example by one of the dynamic confirmatory tests of the OECD, in particular described in OJEC (Official Journal of the European Economic Communities) L 133/106 of 30/05/1988, or by any other equivalent test.

For its use in the form of a softening base, a surfactant according to the invention may be dissolved in one or more solvents chosen from lower alcohols and in particular methanol, ethanol, isopropanol, from glycols and in particular ethylene glycol, propylene glycol, diethylene glycol, dimethylene glycol butyl, propyl, ethyl, methyl ether, diethylene glycol butyl, propyl, ethyl, methyl ether, dipropylene glycol butyl, propyl, ethyl, methyl ether, hexylene glycol, from water and glycerol, but also from the compounds corresponding to the following formula (II):

$(R_5-E)_m-C_j H_{2(j+1)-m-2d+i} O_{k+i}$  (II)

in which:

$R_5$ is a long, saturated or unsaturated hydrocarbon chain having from 5 to 23 carbon atoms E is an

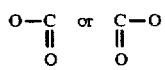

function m is an integer between 1 and 8 j is an integer between 1 and 36 k is an integer or zero i is an integer or zero d is equal to 0, 1 or 2.

In the formula II above:

k represents the number of ether functions in the compound i represents the number of free hydroxyl groups in the compound and d represents the number of unsaturations in the compound, not including those in $R_5$.

The preferred compound II does not comprise free hydroxyl groups, that is to say i is equal to zero.

Advantageously, the compound corresponding to the formula II is chosen from those for which:

m is equal to 1, j is between 1 and 18, and preferably between 1 and 4, and k, i and d are equal to 0, that is to say, in particular, from methyl, ethyl, propyl, isopropyl and butyl esters; for values of m and j equal to 1, $R_5$ is a hydrocarbon chain preferably having 7 to 17 carbon atoms m is equal to 2, j is between 2 and 12 and is preferably equal to 2 or 3, and k, i and d are equal to 0, that is to say, in particular, from ethylene glycol diesters and propylene glycol esters m is equal to 2, j is between 4 and 12, k is equal to 1, i and d are equal to 0 and $R_5$ is a hydrocarbon chain having 7 or 9 carbon atoms, such as the diethylene glycol ester of capric or caprylic acid m is equal to 3, j is equal to 3 or 4, k, i and d are equal to 0 and $R_5$ is a hydrocarbon chain having 7 or 9 carbon atoms, such as the glycerol triester of capric or caprylic acid m is equal to 3, j is equal to 6 and k, i and d are equal to 0, such as trimethylolpropane triester m is equal to 4, j is equal to 5 and k, i and d are equal to 0, such as pentaerythritol tetraester.

The use of a solvent comprising at least one compound corresponding to the formula (II) possesses the following advantages:

in addition to its dissolving power, it provides a lubricating effect and a conditioning effect which are additional to those provided by the surfactant corresponding to the formula (I), the compounds II have a high flash point, enabling that of the resulting surfactant base to be increased, thereby making it safer to use, even at high temperature, the compounds II are biodegradable.

A softening base of the invention advantageously comprises 60 to 99% by weight of at least one compound corresponding to the formula (I) and 40 to 1% by weight of at least one compound of the formula (II) as solvent.

When the softening base comprises more than one surfactant compound, it can comprise a mixture of different surfactant compounds or a mixture of homologous surfactant compounds, independently of the nature of the fatty acids, each of the surfactant compounds corresponding to the formula (I).

Such a mixture may be obtained, either by preparing the two different surfactants separately, or preferably by one and the same condensation reaction of the fatty acid fractions on the one hand and the mixture of different tertiary amines on the other hand.

Another subject of the invention is a softening composition comprising a softening base as described above.

A softening composition of the invention, incorporated in the formula of a textile softener, for example, is stable both chemically, that is to say does not exhibit substantial decomposition when stored at 20° C., and physically, that is to say does not exhibit pronounced phase separation or substantial modifications of the viscosity or odor.

A softening composition according to the invention can, in addition, comprise the additives which are common according to its intended use, such as fragrances, colorings, optical brightening agents, protective agents, etc.

When incorporated in softeners for textile fibers, the compositions of the invention possess viscosities suitable for use in an ordinary domestic washing machine, that is to say less then 700 mPa.s (measured on Contraves TV mobile 3 viscometer, or on any other apparatus giving an equivalent rate of shear).

Any softening composition according to the invention enables a weight concentration of surfactants of between 3 and 30% by weight to be attained in the final product without any problem of presentation and use arising.

When the surfactants which it comprises are obtained by condensation in a single reaction between a fatty acid fraction in the form of glycerol triesters and at least one amine, and then by quaternization, the remainder of said composition comprises byproducts capable of being obtained by the condensation reaction, such as monoglycerides, diglycerides, glycerol, and/or byproducts capable of being obtained by the quaternization reaction, including said product unquaternized.

Lastly, the final subject of the invention is a process for preparing a surfactant.

According to this process, the fatty acids or their ester, anhydride and chloride derivatives, said fatty acids being in free form or in the form of glycerol esters, and preferably glycerol triesters, and said fatty acids corresponding, respectively, to the formulae $R_1COOH$, $R_2COOH$, $R_3COOH$ in which $R_1$, $R_2$, $R_3$ are, respectively, a long, linear or branched alkyl or alkenyl hydrocarbon chain having from 5 to 23 carbon atoms, are reacted with at least one tertiary amine corresponding to the following formula (III):

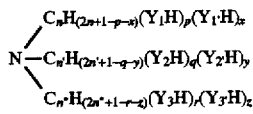

in which:

n, n', n" are non-zero integers, p, q, r, x, y, and z are integers or zero, expressed with reference to one mol, the mean of the sum of n, n' and n" is equal to at least 4, $Y_1$, $Y_{1'}$, $Y_2$, $Y_{2'}$, $Y_3$, $Y_{3'}$ are functional groups, and then in reacting [sic] the condensation product thereby obtained with an alkylating agent, in the presence or absence of a solvent.

It the fatty acids or derivatives are in free form, the process of the invention is characterized by the ratio of the molar concentration of the fatty acids to that of the tertiary amines, which is between 1.85 and 1.40, and in the formula (III) of each tertiary amine, the sum of n, n', n" is between 4 and 12, the sum of p, q, r, x, y and z is statistically on average between 1 and 4, $Y_1$, $Y_{1'}$, $Y_2$, $Y_{2'}$, $Y_3$, $Y_{3'}$ are each chosen from oxy, N and NH groups.

The starting fatty acids are preferably chosen from fatty acids of animal origin such as tallow, and fatty acids of vegetable origin such as those of palm, rapeseed, soybean and sunflower.

The starting tertiary amines, when the sum of p, q, r, x, y and z is greater than 1, are preferably chosen from triethanolamine, methyldiethanolamine, ethyldiethanolamine, dimethylamino-N-(2,3-propanediol), diethylamino-N-(2,3-propanediol), methylamino-N,N-bis (2,3-propanediol) and ethylamino-N,N-bis(2,3-propanediol), and when the sum of p, q, r, x, y and z is equal to 1, they are preferably chosen from dimethylaminopropylamine and dimethylarainoethanolamine, and diethylaminoethanolamine.

According to a preferred implementation of the process, the tertiary amines are mixed, and the mole ratio of tertiary amines for which the sum of p, q, r, x, y and z is strictly greater than 1 to tertiary amines for which the sum of p, q, r, x, y and z is equal to 1 is equal to at least 2.

The alkylating agent is preferably chosen from alkyl halides, sulfates, phosphates and carbonates.

If the fatty acids are in the form of glycerol triesters, the process of the invention is characterized in that the tertiary amine is reacted partially according to a transesterification and/or transesterification/amidation with the glyceride, and:

expressed with reference to one mol, the mean of the sum of n, n' and n" is statistically between 4 and 12, expressed with reference to one mol, the mean of the sum of p, q, r, x, y and z being statistically between 1 and 4, $Y_1$, $Y_{1'}$, $Y_2$, $Y_{2'}$, $Y_3$, $Y_{3'}$ each being chosen from oxy, N and NE groups.

Preferably, the mole ratio of the glycerol triester reacted to that of the tertiary amine is between 1:3 and 1.

In this manner, after quaternization, a softening composition is obtained which has proved to be directly usable, and hence economical to prepare, since, in particular, the abovementioned byproducts which it may contain are for the most part active with respect to the applications in question, and provide additional effects such as a lubricating, suppling, thickening, hydrating effect, while performing in part the role of a solvent.

The process according to the invention is suited to industrialization under economical conditions, on the one hand because it utilizes a starting material that involves little preparation and is abundant, in this instance at least one glycerol triester, or glycerol triester [sic] such as palm oil, and on the other hand because at least one reaction step is limited and hence shorter.

To obtain a softening composition according to the invention according to this process, the mole ratio of the glycerol triester to the tertiary amine is preferably between 1:3 and 1.

The transesterification and/or transesterification/amidation process entails the following additional technical characteristics:

the remainder of the composition or of the surfactant mixture comprises byproducts of the partial reaction, that is to say incomplete quaternization reaction of the condensation product, namely unquaternized (alkyl ester) (and/or amido)amines; some of these products have proved, in effect, to be active, and in some instances surfactant, so that it can be advantageous to limit or control the quaternization reaction, the alkylating agent is preferably chosen from alkyl or alkylbenzyl halides such as methyl chloride or benzyl chloride, alkyl sulfates of the polyalkyl ester sulfate type such as dimethyl or diethyl sulfates, alkyl phosphates, and alkyl carbonates such as dimethyl carbonate, the fatty acids of the glycerol triester preferably comprise at least 50 mol % of linear $C_{16}$ to $C_{18}$ acids.

- the transesterification and/or transesterification/amidation step may or may not be performed in the presence of standard catalysts, in particular acidic or basic catalysts,
- the composition or surfactant mixture may or may not comprise antioxidants, used during the transesterification and/or transesterification/amidation step, in particular butylated hydroxytoluene or butylated hydroxylanisole,
- the composition or surfactant mixture may or may not comprise a decolorizing, reducing or oxidizing agent,
- the composition or surfactant mixture may or may not comprise different modifying or protective agents such as citric acids, tartaric acids, simple or mixed hydrides,
- the composition or surfactant mixture may or may not comprise a complexing agent,
- an additional solvent, in particular of the alcohol, glycol or ester type, may be added to the composition in order to modify its presentation and some of its characteristics,
- as regards the tertiary amine of formula (II) used in the reaction process according to the invention, the sum of the indices p, q, r, x, y and z of the tertiary amine is equal to not more than 4,
- the starting tertiary amine is preferably polyfunctional, that is to say it contains several hydroxyl or primary or secondary amine functions, and is chosen, in particular, from N,N-diethylamino-2,3-propanediol, N,N-dimethylamino-2,3-propanediol, N-ethyldiethanolamine and triethanolamine,
- the tertiary amine is also optionally monofunctional and may also be combined with a polyfunctional amine, that is to say contains a single hydroxyl or primary or secondary amine function, and is, in particular, chosen from the group comprising:
  N,N-dimethylaminopropylamine
  N,N-diethylaminopropylanine
  N,N-dimethylaminoethanolamine
  N,N-diethylaminoethanolamine
  N,N-dimethylaminoisopropanolamine
  N,N-diethylaminoisopropanolamine,
  in this case, the polyfunctional tertiary amine/monofunctional tertiary amine ratio is advantageously between 2 and 200
- the fatty acids selected in the form of glycerol triester are, in particular, oils or fats of natural origin, refined or otherwise, hydrogenated partially, totally or not at all, such as tallow, lard, coconut oil, palm oil, soybean oil, fish oil, rapeseed oil and sunflower oil.

The different subjects of the invention are now dealt with in detail in support of Examples 1 to 15 below, illustrating, in the case of Examples 1 to 8, the preparation of surfactants according to the invention. Examples 1 to 5 corresponding to a preparation from fatty acids in free form or derived (sic), Examples 6 to 8 corresponding to a preparation from fatty acids in the form of glycerol triesters, in the case of Examples 9 to 12, surfactant bases are prepared with a surfactant compound according to the invention, dissolved in a solvent in which at least one compound corresponds to the formula (II), and in the case of Examples 13 to 15, softening compositions according to the invention are prepared.

The process of the invention is not, of course, limited to the working conditions used in these examples, as regards, in particular, the reaction temperatures which can be below 100° C. or above 200° C., and the choice of catalysts and additives, in particular protective or decolorizing additives. The choice of the latter may be made from strong acids, strong bases, alkali metal hydrides, alkali metal alcoholates or those of other metals such as titanium, zinc (titanate, etc.), alkali metal chlorites or hypochlorites, phosphites, hypophosphites, sulfites, hyposulfites or those of other metals or the acid forms where these exist, butylated hydroxytoluene, butylated hydroxyanisole, citrates, tartrates, lactates, gluconates, lactobionates, phosphonates or other complexing agents, without this list being limiting.

In Examples 2, 3, 4, 5 and 10, the overall degree of unsaturation of the collective chains $R_1$, $R_2$, $R_3$ is assessed by the iodine number, which is measured according to AFNOR French Standard NF-ISO 3961 (February 1990) and expressed as grams of iodine per 100 grams of compound tested.

EXAMPLE 1

Preparation of the surfactant referred to as "quat no. 1" consisting of a mixture of compounds corresponding to the formula I in which:

$n+n'+n''=6$ $p+q+r+x+y+z=3$ $Y_1, y_{1'}, Y_2, Y_{2'}, Y_3, Y_{3'}$ are oxy groups $R_4$ represents $CH_3$ $X^-$ represents $CH_3SO_4^-$ Esterification:

540 grams of palm fatty acids are introduced in an inert atmosphere into a stainless steel reactor, and 172 g of triethanolamine are added with stirring. The mixture is heated for at least 12 hours at 140° C. under a partial vacuum in order to remove the water of reaction. The progress of the reaction is monitored by an acid/base assay which determines the residual acidity to obtain an esterification of at least 90 to 95% of the fatty acids.

676 g of a yellow product which is liquid when hot, referred to as "esteramine 1", are recovered, consisting essentially of a mixture of unesterified and mono-, di- and triesterified amine.

Quaternization:

140 g of dimethyl sulfate are added with stirring at a temperature of 60°–80° C. to 676 g of "esteramine 1". After one hour of digestion, the virtually complete absence of residual amine is verified by acid/base assay. 816 g of quaternized esteramine 1 are obtained. The product is then diluted to 90% by adding approximately 11% by weight of isopropanol; 906 g of surfactant referred to as "quat no. 1" are obtained.

EXAMPLE 2

Preparation of the surfactant referred to as "quat no. 2" consisting of a mixture of compounds corresponding to the formula I in which:

$n+n'+n''=6$ $p+q+r+x+y+z=3$ $Y_1, Y_{1'}, Y_2, Y_{2'}, Y_3, Y_{3'}$ are oxy groups $R_4$ represents $CH_3$ $X^-$ represents $CH_3SO_4^-$ Esterification:

493 grams of partially hydrogenated tallow fatty acids, of iodine number 30, are introduced in an inert atmosphere into a stainless steel reactor; 150 g of triethanolamine are added with stirring. The mixture is heated for at least 12 hours at 140° C. under a partial vacuum in order to remove the water of reaction. The progress of the reaction is monitored as before by an acid/base assay which determines the residual acidity. 611 g of a yellow product which is liquid when hot, referred to as "esteramine 2", are recovered, consisting essentially of a mixture of unesterified and mono-, di- and triesterified amine.

Quaternization:

122 g of dimethyl sulfate are added with stirring at a temperature of 60°–80° C. to 611 g of "esteramine 2". After one hour of digestion, the virtually complete absence of residual amine is verified by acid/base assay. 733 g of quaternized esteramine are obtained. The product is then diluted to 90% by adding approximately 11% by weight of isopropanol; 815 g of product referred to as "quat no. 2" are obtained.

EXAMPLE 3

Preparation of the surfactant referred to as "quat no. 3" consisting of a mixture of compounds corresponding to the formula I in which:

$n+n'+n''=6$ $p+q+r+x+y+z=3$ $Y_1, Y_{1'}, Y_2, Y_{2'}, Y_3, Y_{3'}$ are oxy groups $R_4$ represents $CH_3$ $X^-$ represents $CH_3SO_4^-$ Esterification:

544 grams of partially hydrogenated palm fatty acids whose iodine number is about 30 are introduced in an inert atmosphere into a stainless steel reactor. 172 g of triethanolamine are added with stirring. The mixture is heated for at least 12 hours at 140° C., as in Example 1, under a partial vacuum in order to remove the water of reaction. The progress of the reaction is monitored by an acid/base assay which determines the residual acidity. 680 g of a yellow product which is liquid when hot, referred to as "esteramine 3", are recovered, consisting essentially of a mixture of unesterified and mono-, di- and triesterified amine.

Quaternization:

140 g of dimethyl sulfate are added with stirring at a temperature of 60°–80° C. to 680 g of "esteramine 3". After one hour of digestion, the virtually complete absence of residual amine is verified by acid/base assay. 820 g of quaternized esteramine are obtained. The product is diluted to 90% by adding approximately 11% by weight of isopropanol; 911 g of product referred to as "quat no. 3" are obtained.

EXAMPLE 4

Preparation of the surfactant referred to as "quat no. 4" consisting of a mixture of compounds corresponding to the formula I in which:

$n+n'+n''=6$ or 5

$p+q+r+x+y+z=3$ or 1

$Y_1, Y_{1'}, Y_2, Y_{2'}, Y_3, Y_{3'}$ are oxy or NH groups $R_4$ represents $CH_3$ $X^-$ represents $CH_3SO_4^-$ Esterification and amidation:

594.5 grams of partially hydrogenated palm fatty acids whose iodine number is about 30 are introduced in an inert atmosphere into a stainless steel reactor. 172 g of triethanolamine and 18.9 g of dimethylaminopropylamine are added with stirring. The mixture is heated for at least 12 hours at 145° C. under a partial vacuum in order to remove the water of reaction. The progress of the reaction is monitored by an acid/base assay which determines the residual acidity, as in Example 1. 746.1 g of a yellow product which is liquid when hot, referred to as "amine no. 4", are recovered, consisting of a mixture of starting amines, mono-, di- and triesterified amines and alkylamido amine.

Quaternization:

162 g of dimethyl sulfate are added with stirring at a temperature of 60°–80° C. to 746.1 g of the "amine no. 4" described above. After one hour of digestion, the virtually complete absence of residual amine is verified by acid/base assay. 908.1 g of quaternized product are obtained, which product is diluted to 90% by adding approximately 11% by weight of isopropanol. 1009 g of product referred to as "quat no. 4" are obtained.

EXAMPLE 5

Preparation of the surfactant referred to as "quat no. 5" consisting of a mixture of compounds corresponding to the formula I in which:

$n+n'+n''=5$ $p+q+r+x+y+z=2$ or 1

$Y_1, Y_{1'}, Y_2, Y_{2'}, Y_3, Y_{3'}$ are oxy or NH groups $R_4$ represents $CH_3$ $X^-$ represents $CH_3SO_4^-$ Esterification and amidation:

544 grams of partially hydrogenated palm fatty acids whose iodine number is about 30 are introduced in an inert atmosphere into a stainless steel reactor. 137 g of dimethylamino-1,2-propanediol and 18.1 g of dimethylaminopropylamine are added with stirring. The mixture is heated for at least 14 hours at 145° C. under a partial vacuum in order to remove the water of reaction. The progress of the reaction is monitored by an acid/base assay which determines the residual acidity, as in Example 1. 708.2 g of a yellow product which is liquid when hot, referred to as "amine no. 5", are recovered, consisting of a mixture of starting amines, mono- and diesterified amines and amidoamine.

Quaternization:

162.2 g of dimethyl sulfate are added with stirring at a temperature of 60°–80° C. to 708.2 g of the "amine no. 5" described above. After one hour of digestion, the virtually complete absence of residual amine is verified by acid/base assay. 870.4 g of quaternized product are obtained, which product is diluted to 90% by adding approximately 11% by weight of isopropanol. 967.1 g of product referred to as "quat no. 5" are obtained.

EXAMPLE 6

A mixture of 538 g of partially hydrogenated palm oil and 150 g of triethanolamine or TEA is heated under a nitrogen atmosphere for at least 4 h at 140° C. in the presence of 1.5% of sodium methylate until the content of free TEA is less than 6% by weight.

The reaction medium is then treated with 126 g of $Me_2SO_4$. The mixture of quaternary ammonium compounds formed is diluted in isopropyl alcohol to give a dry extract of 80 to 85%, and then decolorized with hydrogen peroxide or a chlorite.

The surfactant agent contained in the mixture thus prepared corresponds statistically to the formula (I) in which:

$n+n'+n''=6$ $p+q+r+x+y+z=3$ $Y_1, Y_{1'}, Y_2, Y_{2'}, Y_3, Y_{3'}$ are oxy groups $R_4=CH_3$
$X^-=CH_3SO_4$

EXAMPLE 7

A mixture of 294 g of palm oil, 5.1 g of dimethylaminopropylamine, 73 g of triethanolamine and 0.2 g of phosphorous acid is heated under a stream of nitrogen at 140° C. to distill off the water of reaction formed. The temperature is gradually increased to 190° C. and then maintained for at least 4 h. At a minimum degree of conversion of 75% of the triethanolamine, the reaction medium is cooled to 60° C. and then quaternized with 62 g of dimethyl sulfate (DMS).

48 g of isopropanol (IPA) are added to adjust the dry extract to 90%. The final active substance, measured according to AFNOR Standard NFT 73-320 (or ISO 2871-1 of May 1989), is then 0.81 mE/g.

The surfactant agent contained in the mixture thus prepared corresponds statistically to the formula (I) in which:

$n+n'+n''=6$ or 5
$p+q+r+x+y+z=3$ or 1
$Y_1$, $Y_{1'}$, $Y_2$, $Y_{2'}$, $Y_3$, $Y_{3'}$ are oxy or NH groups
$R_4=CH_3$
$X^-=CH_3SO_4$

EXAMPLE 8

A mixture of 425 g of palm oil and 110 g of 3-diethylamino-1,2-propanediol is brought to 190° C. with stirring and under a nitrogen atmosphere for 8 h.

At a minimum degree of conversion of 75% of the aminodiol, the reaction medium is cooled to 60° C. and then quaternized with 89 g of DMS. The mixture is heated to 80° C. for 1 h.

The final active substance, measured according to Standard NFT 73-320, is then 0.87 mE/g.

The surfactant agent contained in the mixture thus prepared corresponds to the formula (I) in which:

$n+n'+n''=7$
$p+q+r+x+y+z=2$
$Y_1$, $Y_{1'}$, $Y_2$, $Y_{2'}$, $Y_3$, $Y_{3'}$ are oxy groups
$R_4=CH_3$
$X^-=CH_3SO_4$ Examples 9 to 13 below bring out the advantages of a softening base of the invention comprising at least one surfactant compound corresponding to the formula (I) and a solvent corresponding to the formula (II).

EXAMPLE 9

This example gives the cloud temperatures obtained for surfactant bases of the invention comprising:

compounds of formula I in which, statistically:
$n+n'+n''=6$, $x+y+z=1$
prepared by reaction of two mol of oleic acid with one mol of triethanolamine, followed by reaction of one mol of dimethyl sulfate with the intermediate product obtained, and a compound of formula II in which:
either j=1, m=1, k=i=d=0 and $R_5$ has from 15 to 17 carbon atoms, and the compound II is the methyl ester of palm fatty acid (MEPFA) (formulations 4 and 5)

or j=3, m=2, k=i =d=0 and $R_5$ has 7 or 9 carbon atoms, and the compound II is propylene glycol di(caprate/caprylate, 65:35 m/m) (PGDCC) (formulations 8 and 9)

or j=3, m=3, k=i =d=0 and $R_5$ has 7 or 9 carbon atoms, and the compound II is glycerol tri(caprate/caprylate, 65:35 m/m) (GTCC) (formulations 6 and 7).

or j=3, m=3, k=i =d=0 and $R_5$ has from 5 to 17 carbon atoms, and the compound II is coconut oil (CO) (formulations 2 and 3).

This example enables these cloud temperatures to be compared with those obtained with a surfactant base comprising only the compound I above (formulation I).

The process of determination of the cloud temperature of surfactant bases described in Examples 9 to 12, the objective of which is to determine the temperature corresponding to the start of crystallization of the product, is as follows:

Equipment water bath thermometer graduated in ½° C. divisions standard laboratory glassware Procedure the cationic base is heated beforehand in its solvent to its flow-out temperature approximately 10 g of product are transferred to a 50-ml beaker the product is heated on a waterbath while stirring to a temperature approximately 10° C. above the estimated crystallization point a small portion is transferred to a test tube over 2 to 4 cm, and is cooled at 2° C./min while stirring slowly with a thermometer the crystallization temperature is recorded at the onset of cloudiness at the center of the sample.

The results obtained for the formulations 1 to 9 appear in Table 1 below, in which the concentrations of the compounds I and II are given in percentage by weight.

TABLE 1

| formulation [sic] | 1 | 2 | 3 | 4 | 5 | 6 | 7 | 8 | 9 |
|---|---|---|---|---|---|---|---|---|---|
| Compound I | 100 | 90 | 85 | 90 | 85 | 90 | 85 | 90 | 85 |
| MEPFA | 0 | 0 | 0 | 10 | 15 | 0 | 0 | 0 | 0 |
| PGDCC | 0 | 0 | 0 | 0 | 0 | 0 | 0 | 10 | 15 |
| GTCC | 0 | 0 | 0 | 0 | 0 | 10 | 15 | 0 | 0 |
| CO | 0 | 10 | 15 | 0 | 0 | 0 | 0 | 0 | 0 |
| Cloud temperature (°C.) | >80 | 58 | 45 | 48 | 36 | 54 | 36 | 50 | 28 |

EXAMPLE 10

This example gives the cloud temperatures obtained for surfactant bases of the invention comprising:

compounds of formula I in which, statistically:
$n+n'+n''=6$, $x+y+z=1$
prepared by reaction of two mol of partially hydrogenated tallow fatty acid (iodine number=45 g $I_2$/100 g) with one mol of triethanolamine, followed by reaction of one mol of dimethyl sulfate with the intermediate product obtained, and a compound of formula II in which:
either j=1, m=1, k=i =d=0 and $R_5$ has from 5 to 17 carbon atoms, and the compound II is the methyl ester of coconut fatty acids (MEC) (formulations 11 and 12)

or j=3, m=2, k=i =d=0 and $R_5$ has 7 or 9 carbon atoms, and the compound II is propylene glycol di(caprate/caprylate, 65:35 m/m) (PGDCC) (formulation 13)

or j=3, m=3, k=i =d=0 and $R_5$ has from 5 to 17 carbon atoms, and the compound II is coconut oil (CO) (formulation 16)

or j=5, m=4, k=i d=0 and $R_5$ has 7 or 9 carbon atoms, and the compound II is pentaerythritol tetra(caprate/caprylate, 65:35 m/m) (PETCC) (formulation 14)

or j=6, m=3, k=i =d=0 and $R_5$ has 7 or 9 carbon atoms, and the compound II is trimethylolpropane tri (caprate/caprylate, 65:35 m/m) (TTCC) (formulation 15).

These cloud temperatures are compared with those obtained with a surfactant base comprising only the compound I above (formulation 10) and two conventional surfactant bases comprising the compound I and, as solvent, isopropanol (formulation 17) and dipropylene glycol monomethyl ether (formulation 18), respectively.

The results obtained for the formulations 10 to 19 appear in Table 2 below, in which the concentrations of the compounds I and II are given in percentage by weight.

TABLE 2

| Formulation | 10 | 11 | 12 | 13 | 14 | 15 | 16 | 17 | 18 | 19 |
|---|---|---|---|---|---|---|---|---|---|---|
| Compound I | 100 | 85 | 60 | 80 | 80 | 70 | 70 | 90 | 85 | 80 |
| MEC | 0 | 15 | 40 | 0 | 0 | 0 | 0 | 0 | 0 | 0 |
| PGDCC | 0 | 0 | 0 | 20 | 0 | 0 | 0 | 0 | 0 | 0 |
| PETCC | 0 | 0 | 0 | 0 | 20 | 0 | 0 | 0 | 0 | 0 |
| TTCC | 0 | 0 | 0 | 0 | 0 | 30 | 0 | 0 | 0 | 0 |
| CO | 0 | 0 | 0 | 0 | 0 | 0 | 30 | 0 | 0 | 0 |
| isopropanol | 0 | 0 | 0 | 0 | 0 | 0 | 0 | 10 | 15 | 0 |
| Dipropylene glycol monomethyl ether | 0 | 0 | 0 | 0 | 0 | 0 | 0 | 0 | 0 | 20 |
| Cloud temperature (°C.) | >80 | 58 | 39 | 42 | 66 | 51 | 57 | 41 | 30 | 34 |

EXAMPLE 11

This example gives the cloud temperatures obtained for surfactant bases of the invention comprising:

a compound of formula I in which:
n+n'+n"=7, x=y=z=0 prepared by reaction of two mol of hydrogenated tallow fatty acid with one mol of 1,2-dihydroxy-1-diethylaminopropane, followed by reaction of one mol of dimethyl sulfate with the intermediate product obtained, and a compound of formula II in which:
either j=1, m=1, k=i =d=0 and $R_5$ has 5 or 17 carbon atoms, and the compound is the methyl ester of coconut fatty acids (MEC) (formulations 20, 21 and 22)

or j=3, m=2, k=i =d=0 and $R_5$ has 7 or 9 carbon atoms, and the compound is propylene glycol di(caprate/caprylate, 65:35 m/m) (PGDCC) (formulations 23, 24, 25).

The results obtained for the formulations 20 to 25 appear in Table 3 below, in which the concentrations of the compounds I and II are given in percentage by weight.

TABLE 3

| | formulation | | | | | |
|---|---|---|---|---|---|---|
| | 20 | 21 | 22 | 23 | 24 | 25 |
| Compound I | 90 | 80 | 70 | 90 | 80 | 70 |
| MEC | 10 | 20 | 30 | — | — | — |

TABLE 3-continued

| | formulation | | | | | |
|---|---|---|---|---|---|---|
| | 20 | 21 | 22 | 23 | 24 | 25 |
| PGDCC | — | — | — | 10 | 20 | 30 |
| Cloud temperature (°C.) | 65 | 57 | 53.5 | 63 | 54 | 52 |

Examples 9 and 10 demonstrate the efficacy of the compound II in lowering the cloud temperature of the surfactant base, and in particular for weight concentrations of between 15 and 40% depending on the nature of the compound I.

EXAMPLE 12

Each of the formulations 1 to 25 of Examples 9 to 11 possesses a flash point above 65° C. (determined according to Standard EN57, January 1984).

By way of comparison with a conventional surfactant base, the flash point of the formulations 26 and 27, comprising the compound I defined in any one of Examples 9 to 11 and isopropanol as solvent, was determined according to the same standard as above (Table 4).

TABLE 4

| | Formulation | |
|---|---|---|
| | 26 | 27 |
| Compound I | 90 | 85 |
| Isopropanol | 10 | 15 |
| Flash point (°C.) | 35 | 25 |

EXAMPLE 13

Softener containing 5% of active agent prepared from one of the quaternary ammonium salts no. 1 to 5 obtained according to the invention.

Warm water at 40° C. is introduced into a mixer with stirring, followed by the quaternary ammonium salt at approximately 50° C.; the mixture is stirred until completely homogeneous. It is cooled to 30° C. and the coloring, the fragrance and a preservative are then added according to requirements.

The characteristics of the compositions obtained are presented in Table 5.

TABLE 5

| % m/m | quat no. 1 | quat no. 2 | quat no. 3 | quat no. 4 | quat no. 5 |
|---|---|---|---|---|---|
| % water | 94.2 | 94.2 | 93.9 | 94.1 | 94.1 |
| % quat at 90% concentration in ispropanol | 5.6 | 5.6 | 5.6 | 5.6 | 5.6 |
| % fragrance characteristics | 0.2 | 0.2 | 0.5 | 0.3 | 0.3 |
| natural pH | 3.2 | 2.9 | 3.4 | 3.0 | 3.2 |
| Viscosity 20° C. at time 0 D | 131 | 120 | 60 | 65 | 57 |
| Viscosity 20° C. after 6 days at 50° C. | 153 | 128 | 120 | 90 | 70 |
| Viscosity 20° C. after 20 days at 50° C. | 145 | 157 | 122 | 95 | 68 |

All the viscosities of Examples 13 to 15 are measured at 20° C. using a contraves TV MS $R_2$ viscometer.

EXAMPLE 14

Softener containing 15% or 18% of active agent prepared from one of the quaternary ammonium salts no. 1 to 4 obtained according to the invention.

Warm water at approximately 50° C. is introduced into a mixer with stirring, followed by the quaternary ammonium salt at approximately 50° C. The fluidifying additive is added; the mixture is cooled to 30° C. and the coloring, the fragrance and a preservative are then added according to requirements.

The characteristics of the compositions obtained are presented in Table 6.

TABLE 6

| % m/m | quat no. 1 | quat no. 2 | quat no. 3 | quat no. 4 |
|---|---|---|---|---|
| % water | qs | qs | qs | qs |
| % quat (90% active substance in 10% of isopropanol) | 16.7 | 16.7 | 20 | 20 |
| % $CaCl_2$ (fluidifier) | 0.075 | 0.075 | 0.21 | 0.2 |
| % fragrance | 1.2 | 1.2 | 1.4 | 1.4 |
| characteristics | | | | |
| natural pH | 3.2 | 3.1 | 2.9 | 3.0 |
| Viscosity 20° C. at t = 0 day | 43 | 36 | 36 | 42 |
| Viscosity at 20° C. after 6 days at 50° C. | 37 | 34 | 42 | 45 |
| Viscosity at 20° C. after 20 days at 50° C. | 38 | 52 | 48 | 53 |

EXAMPLE 15

Softener containing 20% of active agent prepared from one of the quaternary ammonium salts no. 1, 3 and 5 obtained according to the invention.

Water at approximately 50° C. is introduced into a mixer with stirring, followed by the quaternary ammonium salt at approximately 50° C. The mixture is stirred until completely homogeneous; it is cooled to 35°–38° C. The fluidifying additive is added, and the coloring, the fragrance and a preservative are then added according to requirements.

The characteristics of the compositions obtained are presented in Table 7.

TABLE 7

| % m/m | quat no. 1 | quat no. 3 | quat no. 5 |
|---|---|---|---|
| water | qs | | |
| quat (at 90% concentration in isopropanol) | 22.22 | 22.25 | 22.25 |
| quat TEA/DMS* (fluidifier) | 0.7 | 0 | 0.8 |
| $CaCl_2$(fluidifier) | 0 | 0.24 | 0 |
| Fragrance | 0.8 | 1.4 | 0.9 |
| Characteristics | | | |
| natural pH | 2.9 | 3.5 | 3.4 |
| Viscosity at 20° C. | 56 | 46 | 110 |
| Viscosity after 6 days at 50° C. | 56 | 82 | 180 |
| Viscosity after 20 days at 50° C. | 56 | 100 | 170 |

*TEA/DMS is the quaternary ammonium salt obtained by reaction of one mol of dimethyl sulfate with one mole of triethanolamine.

We claim:

1. A softening composition comprising at least one quaternary ammonium salt prepared by quaternizing the product of the condensation reaction between a fatty acid fraction containing at least one saturated or unsaturated, linear or branched fatty acid, or derivative thereof, said fatty acids or derivatives having a hydrocarbon chain in which the number of atoms is between 5 and 23, and at least one functionalized tertiary amine, the sum of the carbon atoms in the alkyl chains of said tertiary amine being from 4–12, and the alkyl chains including from one to four functional groups selected from the group consisting of hydroxyl and amino, wherein the molar ratio of the fatty acid fraction to tertiary amine is from about 1.85:1 and 1.40:1 dissolved in a solvent.

2. A softening composition according to claim 1, wherein it comprises as solvent at least one compound corresponding to the following formula:

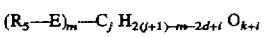

in which:

$R_5$ is a long, saturated or unsaturated hydrocarbon chain having from 5 to 23 carbon atoms E is an

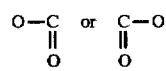

function m is an integer between 1 and 8 j is an integer between 1 and 36 k is an integer or zero i is an integer or zero d is equal to 0, 1 or 2.

3. A softening composition according to claim 2, wherein i is equal to 0.

4. A softening composition according to claim 3, wherein that, if m is equal to 1, j is between 1 and 18, and preferably between 1 and 4, and k and d are equal to 0.

5. A softening composition according to claim 4, wherein, if j is equal to 1, $R_5$ is a hydrocarbon chain having from 7 to 17 carbon atoms.

6. A softening composition according to claim 3, wherein, if m is equal to 2, k and d are equal to 0 and j is between 2 and 12.

7. A softening composition according to claim 3, wherein, if m is equal to 2, k is equal to 1, j is between 4 and 12, d is equal to 0 and $R_5$ is a hydrocarbon chain having 7 or 9 carbon atoms.

8. A softening composition according to claim 3, wherein, if m is equal to 3, j is equal to 3 or 4, k and d are equal to 0 and $R_5$ is a hydrocarbon chain having 7 or 9 carbon atoms.

9. A softening composition according to claim 3, wherein, if m is equal to 3, j is equal to 6 and k and d are equal to 0.

10. A softening composition according to claim 3, wherein, if m is equal to 4, j is equal to 5 and k and d are equal to 0.

* * * * *